(12) United States Patent
Nielsen

(10) Patent No.: US 6,663,903 B1
(45) Date of Patent: Dec. 16, 2003

(54) METHODS FOR USING XYLOGLUCAN ENDOTRANSGLYCOSYLASE IN BAKING

(75) Inventor: Ruby Ilum Nielsen, Farum (DK)

(73) Assignee: Novozymes A/S, Bagsvaerd (DK)

( * ) Notice: Subject to any disclaimer, the term of this patent is extended or adjusted under 35 U.S.C. 154(b) by 114 days.

(21) Appl. No.: 09/703,011

(22) Filed: Oct. 31, 2000

Related U.S. Application Data

(63) Continuation of application No. PCT/DK99/00277, filed on May 21, 1999.
(60) Provisional application No. 60/088,096, filed on Jun. 5, 1998.

(30) Foreign Application Priority Data

May 29, 1998 (DK) ........................................ 1998 00749

(51) Int. Cl.[7] ........................... A21D 8/02; A21D 10/00; A21D 2/00; A21D 2/08; C12N 9/04; C12N 9/20; C12N 9/26; C12N 9/42; C12N 9/50; C12N 9/88
(52) U.S. Cl. ........................... 426/61; 426/62; 426/549; 426/19; 426/20; 426/556; 426/552; 435/200; 435/201; 435/209; 435/212; 435/190; 435/198; 435/219; 435/232
(58) Field of Search ........................... 426/61, 62, 549, 426/19, 20, 556, 552; 435/200, 201, 209, 212, 190, 198, 219, 232

(56) References Cited

FOREIGN PATENT DOCUMENTS

| | | |
|---|---|---|
| EP | 0 562 836 A1 | 3/1993 |
| WO | WO 95/13384 | 5/1995 |
| WO | WO 97/23683 | 7/1997 |
| WO | WO9723683 * | 7/1997 .......... D06M/16/00 |
| WO | WO 98/38288 | 9/1998 |

OTHER PUBLICATIONS

WPI, Derwent accession No. 95–380073, Dainippon Pharm Co Ltd: "A Protein–xylo–glucan complex –prepd. By combining protein with xylo–glucan using aminocarbonyl reaction".

CAPLUS accession No. 1992: 422231, Document No. 117:22231, Fry, Stephen c. et al.: "Xyloglucan endotransglycosylase, a new wall–loosening enzyme activity from plants" Biochem.J. (1992) 282:821–828.

* cited by examiner

Primary Examiner—Rebecca E. Prouty
Assistant Examiner—Sheridan Swope
(74) Attorney, Agent, or Firm—Jason I. Garbell; Elias J. Lambiris

(57) ABSTRACT

The present invention relates to methods for preparing a dough, comprising incorporating into the dough a composition comprising an effective amount of an XET which improves one or more properties of the dough or a baked product obtained from the dough. The present invention also relates to methods for preparing a baked product. The present invention also relates to compositions comprising an effective amount of an XET for improving one or more properties of a dough and/or a baked product obtained from the dough. The present invention further relates to doughs or baked products and to pre-mixes for a dough.

13 Claims, No Drawings

SEQUENCE LISTING

<160> NUMBER OF SEQ ID NOS: 2

<210> SEQ ID NO 1
<211> LENGTH: 975
<212> TYPE: DNA
<213> ORGANISM: Tiarosporella phaseolina
<220> FEATURE:
<221> NAME/KEY: CDS
<222> LOCATION: (45)...(779)

<400> SEQUENCE: 1

```
ggatccgaat tccaactatc ctgccctcct ttcaagcgaa cacc atg aag ttc tcc        56
                                                Met Lys Phe Ser
                                                  1 tcg gct ctg ttt ctg gcc gct acg gcg gtc ttg gct tcc gcc gcg ccg       104
Ser Ala Leu Phe Leu Ala Ala Thr Ala Val Leu Ala Ser Ala Ala Pro
  5              10                  15                  20 ctt gag cgc cgc gcc gac ttt tgt ggt caa tgg gac aac gtg aag aac       152
Leu Glu Arg Arg Ala Asp Phe Cys Gly Gln Trp Asp Asn Val Lys Asn
                 25                  30                  35 gga cct tac act ctt tac aac aac ctg tgg gga aaa gat gct tcc gga       200
Gly Pro Tyr Thr Leu Tyr Asn Asn Leu Trp Gly Lys Asp Ala Ser Gly
             40                  45                  50 gcc tcc gga tcg caa tgc acc ggc gtc gat agc ttc agc agc aac acc       248
Ala Ser Gly Ser Gln Cys Thr Gly Val Asp Ser Phe Ser Ser Asn Thr
         55                  60                  65 atc gct tgg cac aca tcc tgg tcc tgg tcc ggt gct cag tac aat gtc       296
Ile Ala Trp His Thr Ser Trp Ser Trp Ser Gly Ala Gln Tyr Asn Val
     70                  75                  80 aag tct tac gca aac gtg gtc gtc gac atc acc tct aag aaa ctc agc       344
Lys Ser Tyr Ala Asn Val Val Val Asp Ile Thr Ser Lys Lys Leu Ser
 85                  90                  95                 100 gcc atc agc agc att aac agc atc tgg cgc tgg gct tac acg ggt agc       392
Ala Ile Ser Ser Ile Asn Ser Ile Trp Arg Trp Ala Tyr Thr Gly Ser
                105                 110                 115 aac att gtt gcc aat gtt gcc tac gat atc ttc act tca tcc act gtc       440
Asn Ile Val Ala Asn Val Ala Tyr Asp Ile Phe Thr Ser Ser Thr Val
            120                 125                 130 ggt ggt agc gag gaa tat gaa atc atg ata tgg gtt ggt gct ctc ggt       488
Gly Gly Ser Glu Glu Tyr Glu Ile Met Ile Trp Val Gly Ala Leu Gly
        135                 140                 145 ggt gct ggt ccg atc tca tct acc ggc tcc cct att gcc acc gtt tcc       536
Gly Ala Gly Pro Ile Ser Ser Thr Gly Ser Pro Ile Ala Thr Val Ser
    150                 155                 160 ctt gca ggc tcc tcg tgg aag ctc tac aaa ggg ccc aac ggg cag atg       584
Leu Ala Gly Ser Ser Trp Lys Leu Tyr Lys Gly Pro Asn Gly Gln Met
165                 170                 175                 180 acc gtg ttc agc ttc gtc gcc gag tcc aac gtg aac aac ttc agc ggt       632
Thr Val Phe Ser Phe Val Ala Glu Ser Asn Val Asn Asn Phe Ser Gly
                185                 190                 195
```

```
gac ctt aac gct ttc atc aag tac ctc acc ggc aac cag ggc ctt ccc      680
Asp Leu Asn Ala Phe Ile Lys Tyr Leu Thr Gly Asn Gln Gly Leu Pro
            200                 205                 210 gcc tcg caa tac atc aag agc att ggc gct ggc act gag ccg ttc acg      728
Ala Ser Gln Tyr Ile Lys Ser Ile Gly Ala Gly Thr Glu Pro Phe Thr
        215                 220                 225 ggt tcc aac gcc aag ctg acc act tcc tcc tac act gtc agc ttc aga      776
Gly Ser Asn Ala Lys Leu Thr Thr Ser Ser Tyr Thr Val Ser Phe Arg
    230                 235                 240 taa ctgtgaagct ttatgctgcc cttatgcatc atccttgtac atagttatca           829
* ccagggact cttgtaaata cgattgcctt attaaccgcc tgcatctgct ttcacacaat     889
ggcatttacc aatcaacagt gcgcctcgaa tccgtaaaag gtggcttaaa aaaaaaaaa     949 aaaaaaaaaa aaattcctgc ggccgc                                        975

<210> SEQ ID NO 2
<211> LENGTH: 244
<212> TYPE: PRT
<213> ORGANISM: Tiarosporella phaseolina

<400> SEQUENCE: 2

Met Lys Phe Ser Ser Ala Leu Phe Leu Ala Ala Thr Ala Val Leu Ala
1               5                   10                  15

Ser Ala Ala Pro Leu Glu Arg Arg Ala Asp Phe Cys Gly Gln Trp Asp
            20                  25                  30

Asn Val Lys Asn Gly Pro Tyr Thr Leu Tyr Asn Asn Leu Trp Gly Lys
        35                  40                  45

Asp Ala Ser Gly Ala Ser Gly Ser Gln Cys Thr Gly Val Asp Ser Phe
    50                  55                  60

Ser Ser Asn Thr Ile Ala Trp His Thr Ser Trp Ser Trp Ser Gly Ala
65                  70                  75                  80

Gln Tyr Asn Val Lys Ser Tyr Ala Asn Val Val Asp Ile Thr Ser
                85                  90                  95

Lys Lys Leu Ser Ala Ile Ser Ser Ile Asn Ser Ile Trp Arg Trp Ala
            100                 105                 110

Tyr Thr Gly Ser Asn Ile Val Ala Asn Val Ala Tyr Asp Ile Phe Thr
        115                 120                 125

Ser Ser Thr Val Gly Gly Ser Glu Glu Tyr Glu Ile Met Ile Trp Val
    130                 135                 140

Gly Ala Leu Gly Gly Ala Gly Pro Ile Ser Ser Thr Gly Ser Pro Ile
145                 150                 155                 160

Ala Thr Val Ser Leu Ala Gly Ser Ser Trp Lys Leu Tyr Lys Gly Pro
                165                 170                 175

Asn Gly Gln Met Thr Val Phe Ser Phe Val Ala Glu Ser Asn Val Asn
            180                 185                 190

Asn Phe Ser Gly Asp Leu Asn Ala Phe Ile Lys Tyr Leu Thr Gly Asn
        195                 200                 205

Gln Gly Leu Pro Ala Ser Gln Tyr Ile Lys Ser Ile Gly Ala Gly Thr
    210                 215                 220

Glu Pro Phe Thr Gly Ser Asn Ala Lys Leu Thr Thr Ser Ser Tyr Thr
225                 230                 235                 240

Val Ser Phe Arg
```

METHODS FOR USING XYLOGLUCAN ENDOTRANSGLYCOSYLASE IN BAKING

CROSS-REFERENCE TO RELATED APPLICATIONS

This application is a continuation application of PCT/DK99/00277 filed May 21, 1999 and claims priority under 35 U.S.C. 119 of Danish application 98/0749, filed May 29, 1998, and of U.S. Provisional application No. 60/088,096, filed Jun. 5, 1998, the contents of which are fully incorporated herein by reference.

FIELD OF THE INVENTION

The present invention relates to methods for preparing a dough and/or baked product with a xyloglucan endotransglycosylase.

BACKGROUND ART

The strength of a dough is an important aspect of baking for both small-scale and large-scale applications. A strong dough has a greater tolerance of mixing time, proofing time, and mechanical vibrations during dough transport, whereas a weak dough is less tolerant to these treatments. A strong dough with superior rheological and handling properties results from flour containing a strong gluten network. Flour with a low protein content or a poor gluten quality results in a weak dough.

Dough "conditioners" are well known in the baking industry. The addition of conditioners to bread dough has resulted in improved machinability of the dough and improved texture, volume, flavour and freshness (increased resistance to staling) of the bread. Nonspecific oxidants, such as iodates, peroxides, ascorbic acid, potassium bromate and azodicarbonamide have a gluten strengthening effect. It has been suggested that these conditioners induce the formation of interprotein bonds which strengthen the gluten, and thereby the dough. However, the use of several of the currently available chemical oxidizing agents has been met with consumer resistance or is not permitted by regulatory agencies.

The use of enzymes as dough conditioners has been considered as an alternative to the chemical conditioners. A number of enzymes have been used recently as dough and/or bread improving agents, in particular, enzymes which act on components present in large amounts in the dough. Examples of such enzymes are found within the groups of amylases, proteases, glucose oxidases, and (hemi)cellulases, including pentosanases.

Xyloglucan endotransglycosylase (XET) is an enzyme which catalyses an endo-transglycosylation of xyloglucan, a structural polysaccharide of plant cell walls. The enzyme is believed to be present in all plants, and in particular, land plants. XET has been extracted from dicotyledons, monocotyledons, such as graminaceous monocotyledons and liliaceous monocotyledons, and also from a moss and a liverwort (Fry, S., et al., 1992. *Biochem. J.* 282: 821–828).

XET may be obtained from a plant as described in WO 95/13384, WO 97/23683, or EP 562 836, or it may be obtained as described by Fry, et al., op cit.

It is the object of the present invention to improve the properties of dough and/or baked products by the use of an XET.

SUMMARY OF THE INVENTION

The present invention relates to methods for preparing a dough and a baked product made from dough, respectively, comprising incorporating into the dough an effective amount of a xyloglucan endotransglycosylase (XET).

The present invention also relates to methods for preparing a baked product.

The present invention also relates to compositions comprising an effective amount of one or more XETs, for improving one or more properties of a dough and/or a baked product obtained from the dough, and a carrier and/or a baking ingredient.

The present invention also relates to doughs and to baked products, respectively.

The present invention further relates to pre-mixes for a dough comprising an effective amount of an XET for improving one or more properties of a dough and/or a baked product obtained from the dough, and a carrier and/or a baking ingredient.

DETAILED DESCRIPTION OF THE INVENTION

The present invention relates to methods for preparing a dough or a baked product made from dough comprising incorporating into the dough an effective amount of an XET which improves one or more properties of the dough or the baked product obtained from the dough relative to a dough or a baked product in which XET is not incorporated.

In the methods of the present invention, an XET is incorporated into the dough by adding the XET to the dough, to any single ingredient from which the dough is to be made, and/or to any mixture of dough ingredients from which the dough is to be made. In other words, the XET may be added in any step of the dough preparation and may be added in one, two, or more steps.

The term "effective amount" is defined herein as an amount of an XET which is sufficient for providing a measurable effect on at least one property of interest of the dough and/or baked product.

The term "improved property" is defined herein as any property of a dough and/or a product obtained from the dough, particularly a baked product, which is improved by the action of an XET relative to a dough or product in which an XET is not incorporated. The improved property may include, but is not limited to, increased strength of the dough, increased elasticity of the dough, increased stability of the dough, reduced stickiness of the dough, improved extensibility of the dough, improved machinability of the dough, increased volume of the baked product, improved crumb structure of the baked product, improved softness of the baked product, improved flavour of the baked product, and/or improved antistaling of the baked product.

The use of an XET may result in an increased strength, stability, and/or reduced stickiness of the dough, resulting in improved machinability, as well as in an increased volume and improved crumb structure and softness of the baked product. The effect on the dough may be particularly advantageous when a poor quality flour is used. The improved machinability is of particular importance in connection with dough which is to be processed industrially.

The improved property may be determined by comparison of a dough and/or a baked product prepared without addition of an XET in accordance with the methods of the present invention. Techniques which can be used to determine improvements achieved by use of the methods of present invention are described below in the Examples. Organoleptic qualities may be evaluated using procedures well established in the baking industry, and may include, for example, the use of a panel of trained taste-testers.

The term "increased strength of the dough" is defined herein as a the property of dough which has generally more elastic properties and/or requires more work input to mould and shape.

The term "increased elasticity of the dough" is defined as the property of a dough which has a higher tendency to regain its original shape after being subjected to a certain physical strain.

The term "increased stability of the dough" is defined herein as the property of a dough that is less susceptible to mechanical abuse thus better maintaining its shape and volume.

The term "reduced stickiness of the dough" is defined herein as the property of a dough that has less tendency to adhere to surfaces, e.g., in the dough production machinery, and is either evaluated empirically by the skilled test baker or measured by the use of a texture analyzer (e.g., TAXT2) as known in the art.

The term "improved extensibility of the dough" is defined as the property of a dough that can be subjected to increased strain or stretching without rupture.

The term "improved machinability of the dough" is defined herein as the property of a dough that is generally less sticky and/or more firm and/or more elastic.

The term "increased volume of the baked product" is measured as the specific volume of a given loaf of bread (volume/weight) determined typically by the traditional rapeseed displacement method.

The term "improved crumb structure of the baked product" is defined herein as the property of a baked product with finer and/or thinner cell walls in the crumb and/or more uniform/homogenous distribution of cells in the crumb and is usually evaluated empirically by the skilled test baker.

The term "improved softness of the baked product" is the opposite of "firmness" and is defined herein as the property of a baked product that is more easily compressed and is evaluated either empirically by the skilled test baker or measured by the use of a texture analyzer (e.g., TAXT2) as known in the art.

The term "improved flavour of the baked product" is evaluated as mentioned above by a trained test panel.

The term "improved antistaling of the baked product" is defined herein as the properties of a baked product that has a reduced rate of deterioration of quality parameters, e.g., softness and/or elasticity, during storage.

In a preferred embodiment, the XET improves one or more properties of the dough or the baked product obtained from the dough. In another preferred embodiment, the XET improves one or more properties of the dough and the baked product obtained from the dough.

In a preferred embodiment, the improved property is increased strength of the dough. In another preferred embodiment, the improved property is increased elasticity of the dough. In another preferred embodiment, the improved property is increased stability of the dough. In another preferred embodiment, the improved property is reduced stickiness of the dough. In another preferred embodiment, the improved property is improved extensibility of the dough. In another preferred embodiment, the improved property is improved machinability of the dough. In another preferred embodiment, the improved property is increased volume of the baked product.

In another preferred embodiment, the improved property is improved crumb structure of the baked product. In another preferred embodiment, the improved property is improved softness of the baked product. In another preferred embodiment, the improved property is improved flavour of the baked product.

In another preferred embodiment, the improved property is improved antistaling of the baked product.

The term "dough" is defined herein as a mixture of flour and other ingredients firm enough to knead or roll. The dough may be fresh, frozen, par-baked, or pre-baked. Preferably, the dough of the present invention is fresh or par-baked, i.e., the dough is preferably baked without being frozen. The preparation of frozen dough is described by Kulp and Lorenz in *Frozen and Refrigerated Doughs and Batters*.

The term "baked product" is defined herein as any product prepared from dough, either of a soft or a crisp character. Examples of baked products, whether of a white, light or dark type, which may advantageously be produced by the present invention are bread (in particular white, whole-meal or rye bread), typically in the form of loaves or rolls, French baguette-type bread, noodles, pasta, pizzas, pita bread, tortillas, tacos, cakes, pancakes, biscuits, cookies, pie crusts, steamed bread, and crisp bread, and the like.

The XET may be any XET which provides an improved property to a dough and/or to a baked product obtained from the dough.

The term "xyloglucan endotransglycosylase (XET)" as used in the present invention is defined herein as glycosyl-transferase which has the capacity to transfer a high molecular weight portion from a donor xyloglucan to a suitable acceptor such as a xyloglucan-derived monosaccharide.

Examples of an XET useful in the methods of the present inventions are described in PCT/DK98/00076, WO 95/13384 and WO 97/23683.

In the methods of the present invention, any XET may be used which possesses suitable enzyme activity in a pH and temperature range appropriate for making a dough and/or a baked product. It is preferable that the XET is active over broad pH and temperature ranges.

In a preferred embodiment, the XET has a pH optimum in the range of about 3 to about 10. In a more preferred embodiment, the XET has a pH optimum in the range of about 4.5 to about 8.5.

In a preferred embodiment, the XET has a temperature optimum in the range of about 5° C. to about 100° C. In a more preferred embodiment, the XET has a temperature optimum in the range of about 25° C. to about 75° C.

The source of the XET to be used according to the present invention is not critical for improving one or more properties of a dough and/or a baked product. Accordingly, the XET may be obtained from any source such as a plant, microorganism, or animal. The XET is preferably obtained, e.g., from a microbial source, such as a bacterium or a fungus, e.g., a filamentous fungus or a yeast.

In a preferred embodiment, the XET is obtained from a plant source. For example, the XET may be obtained from a dicotyledon or a monocotyledon, in particular a dicotyledon selected from the group consisting of cauliflowers, soy beans, tomatoes, potatoes, rapes, sunflowers, cotton, and tobacco, or a monocotyledon selected from the group consisting of wheat, rice, corn and sugar cane.

In another preferred embodiment, the XET is obtained from a fungal source, and more preferably from a fungus from a Basidiomycota, Zygomycota, Ascomycota or Mitosporic strain.

A preferred Basidiomycota strain is a Hymenomycetes strain belonging to the orders Coriolales, Schizophyllales, Stereales or Xenasmatales; in particular a strain belonging to one of the families Coriolaceae, Corticiaceae, Schizophyllaceae, Stereaceae or Tubulicrinaceae. Preferred genera is one of the following: Trametes, Corticium, Schizophyllum, or Tubulicrinis. A preferred species is one of the following: *Trametes hirsuta, Corticium roseum*, Schizophyllum sp, *Stereum hirsutum* or *Tubulicrinis subulatus*.

Preferred Ascomycota are strains belonging to the classes Loculoascomycetes, Discomycetes, Pyrenomycetes, and Plectomycetes, preferably those belonging to the orders Dothideales, Rhytismatales, Pezizales, Leotiales, Xylariales, Hypocreales, Halosphaeriales, Phyllachorales, Diaporthales and Eurotiales.

Preferred strains are strains belonging to the families Botryosphaeriaceae, Dothioraceae, Mycosphaerellaceae, Tubeufiaceae, Pleosporaceae, Leptosphaeriaceae, Rhytismataceae, Sarcosomataceae, Pyronemataceae, Ascobolaceae, Sclerotiniaceae, Amphisphaeriaceae, Xylariaceae, Hypocreaceae, Halosphaeriaceae, Phyllachoraceae, Valsaceae, Melanconidaceae and Trichocomataceae; especially strains belonging to the genera Diplodia, Plowrightia, Phyllosticta, Septoria, Tubeufia, Alternaria, Coniothyrium, Phoma, Embellisia, Tiarosporella, Galiella, Pseudoplectania, Pyronema, Oedocephalum, Botrytis, Aposphaeria, Pestalotia, Pestalotiopsis, Poronia, Nodulisporium, Xylaria, Fusarium, Verticillium, Volutella, Chaetapiospora, Lulworthia, Colletotrichum, Cytospora, Discula, Phomopsis, Coryneum, Seimatosporium, Aspergillus, Eurotium, Eupenicillium, Penicillium, Petromyces and Talaromyces.

In another preferred embodiment the XET is obtained from a *Diplodia gossypina, Plowrightia ribesia*, Phyllosticta sp, Septoria sp, *Tubeufia amazonensis*, Alternaria sp, *Embellisia hyacinthi, Phoma neoloba, Phoma tropica*, Coniothyrium sp, *Coniothyrium olivaceoum, Coniothyrium dunckii, Galiella celebica, Pseudoplectania nigrella, Pyronema domesticum*, Oedocephalum sp, *Botrytis cinerea*, Aposphaeria sp, Pestalotia sp, Pestalotiopsis sp. *Poronia punctata*, Xylaria sp, Nodulisporium sp, *Fusarium solani*, Verticillium sp, *Volutella buxi, Chaetapiospora rhododendri, Lulworthia uniseptata, Colletotrichum aculatum, Colletotrichum crassipes*, Cytospora spp, Discula sp, *Phomopsis ilicis, Phomopsis cirsii, Coryneum castaneicola, Seimatosporium lichenicola, Aspergillus tamarii, Eurotium chevalieri, Eupenicillium javanicum, Penicillium capsulatum, Penicillium olsonii, Penicillium pinophilum, Penicillium roqueforti, Penicillium italicum, Penicillium canescens, Penicillium verruculosum, Petromyces alliaceus* and *Talaromyces flavus*.

In another preferred embodiment the XET is obtained from a strain of Tiarosporella. In an even more preferred embodiment the XET is obtained from a strain of *Tiarosporella phaseolina*, or a synonym or teleomorph thereof. A strain of *Tiarosporella phaseolina* (Macrophomina sp., Classification: Ascomycota, Discomycetes, Rhytismatales, Rhytismataceae) has been deposited according to the Budapest Treaty on the International Recognition of the Deposits of Microorganisms for the Purpose of Patent Procedures, on Jan. 28, 1997, at Centraalbureau voor Schimmelcultures (CBS) under Accession No. CBS 446.97. In a most preferred embodiment the XET is obtained from *Tiarosporella phaseolina* CBS No. 446.97.

Examples of useful Zygomycota are strains belonging to the order Mucorales, preferably strains belonging to the families Chaetocladiaceae and Mucoraceae.

Preferred strains belong to the genera Dichotomocladium, Actinomucor, Gongronella, Sporodiniella and Mucor, in particular *Dichotomocladium hesseltinei, Actinomucor elegans, Gongronellla butleri, Sporodiniella umbellata* and *Mucor miehei* var minor.

An example of a strain of uncertain taxonomy from which an XET may be obtained is *Vialaea insculpta*.

Examples of strains belonging to the Mitosporic fungi are *Acrodontium crateriforme, Aureobasidium pullulans*, Circinotrichum sp, Cryptocline sp. Ellisiopsis sp, *Epicoccum nugrum*, Gliocladium sp, *Helicorhoidion irregulare*, Hendersonia spp, Mariannaea sp, Microsphaeropsis sp, Ramularia sp, Sarcopodium sp, Spadicoides sto, *Speiropsis pedatospora, Sporotrichum exile*, Stilbella sp, Trichothecium sp, *Trimmatostroma abietes, Tubakia dryina*, Wiesneriomyces sp and *Zygosporium masonii*.

In a preferred embodiment, the XET is obtained from a bacterial source. For example, the XET may be obtained from a gram-negative or gram-positive bacterial cell.

Examples of XET-producing gram-positive bacteria are strains belonging to the genus Bacillus.

In another preferred embodiment, the XET may be obtained from the following strains which have been found to be XET-positive:

1. *Dichotomocladium hesseltinei*. Acc No of strain: CBS 164.61. Classification: Zygomycota, Mucorales, Chaetocladiaceae.
2. *Actinomucor elegans*. Ex of Acc No of strain: CBS 154.86. Classification: Zygomycota, Mucorales, Chaetocladiaceae.
3. *Mucor miehei* var minor. Acc No of strain: ATCC 36018. Classification: Zygomycota, Mucorales, Mucoraceae.
4. *Gongronella butleri*. A strain of *Gongronella butleri* has been deposited according to the Budapest Treaty on the International Recognition of the Deposits of Microorganisms for the Purpose of Patent Procedures, on Jan. 28, 1997, at Centraalbureau voor Schimmelcultures (CBS), under Accession No. CBS 448.97. Classification: Zygomycota, Mucorales, Chaetocladiaceae.
5. *Sporodiniella umbellata*. Acc No of strain: CBS 195.77. Classification: Zygomycota, Mucorales, Mucoraceae.
6. Phyllosticta sp. Isolated from a leaf of Pithecolobium sp., China. Classification: Ascomycota, Loculoascomycetes, Dothidiales, Mycosphaellaceae.
7. Septoria sp. A strain of Septoria sp has been deposited according to the Budapest Treaty on the International Recognition of the Deposits of Microorganisms for the Purpose of Patent Procedures, on Jan. 2, 1996, at Centraalbureau voor Schimmelcultures (CBS), under Accession No. CBS 831.95. Classification: Ascomycota, Loculoascomycetes, Dothidiales, Mycosphaellaceae.
8. *Diplodia gossypina*. A strain of *Diplodia gossypina* has been deposited according to the Budapest Treaty on the International Recognition of the Deposits of Microorganisms for the Purpose of Patent Procedures, on Mar. 12, 1996, at Centraalbureau voor Schimmelcultures (CBS), under Accession No. CBS 274.96. Classification: Ascomycota, Loculoascomycetes, Dothidiales, Botrysphaeriaceae.
9. *Plowrightia ribesia*. Isolated from Ribes sp., Denmark. Classification: Ascomycota, Loculoascomycetes, Dothidiales, Dothioraceae.
10. *Tubeufia amazonensis*. Acc No of Strain: ATCC 42524. Classification: Ascomycota, Loculoascomycetes, Dothidiales, Tubeufiaceae.

11. Alternaria sp. Classification: Ascomycota, Loculoascomycetes, Dothidiales, Pleosporaceae.
12. *Embellisia hyacinthi*. Acc No of species IMI 211561. Classification: Ascomycota, Loculoascomycetes, Dothidiales, Pleosporaceae.
13. *Phoma neoloba*. Classification: Ascomycota, Loculoascomycetes, Dothideales, Pleosporaceae.
14. *Phoma tropica*. Ex on Acc No of species CBS 537.66. Classification: Ascomycota, Loculoascomycetes, Dothideales, Pleosporaceae.
15. Coniothyrium sp. Classification: Ascomycota, Loculoascomycetes, Dothideales, Leptosphaeriaceae.
16. *Coniothyrium olivaceoum*. Ex on Acc No of species CBS 304.68. Classification: Ascomycota, Loculoascomycetes, Dothideales, Leptosphaeriaceae.
17. *Coniothyrium dunckii*. Classification: Ascomycota, Loculoascomycetes, Dothideales, Leptosphaeriaceae.
18. Tiarosporella sp. Classification: Ascomycota, Discomycetes, Rhytismatales, Rhytismataceae.
19. *Galiella celebica*. Isolated from a sample collected in Japan. Classification: Ascomycota, Discomycetes, Pezizales, Sarcosomataceae.
20. *Pseudoplectania nigrella*. A strain of *Pseudoplectania nigrella* has been deposited according to the Budapest Treaty on the International Recognition of the Deposits of Microorganisms for the Purpose of Patent Procedures, on Jan. 28, 1997, at Centraalbureau voor Schimmelcultures (CBS), under Accession No. CBS 444.97. Classification: Ascomycota, Discomycetes, Pezizales, Sarcosomataceae.
21. *Pyronema domesticum*. Isolated from a sample collected in Norway. Classification: Ascomycota, Discomycetes, Pezizales, Pyronemataceae.
22. Oedocephalum sp. Classification: Ascomycota, Discomycetes, Pezizales, Ascobolaceae.
23. *Botrytis cinerea*. A strain of *Botrytis cinerea* has been deposited according to the Budapest Treaty on the International Recognition of the Deposits of Microorganisms for the Purpose of Patent Procedures, on Jan. 28, 1997, at Centraalbureau voor Schimmelcultures (CBS), under Accession No. CBS 447.97. Classification: Ascomycota, Discomycetes, Leotiales, Sclerotiniaceae.
24. Aposphaeria sp. Classification: Ascomycota, Discomycetes, Leotiales, Sclerotiniaceae.
25. Pestalotia sp. A strain of Pestalotia sp. has been deposited according to the Budapest Treaty on the International Recognition of the Deposits of Microorganisms for the Purpose of Patent Procedures, on Jan. 28, 1997, at Centraalbureau voor Schimmelcultures (CBS), under Accession No. CBS 445.97. Classification: Ascomycota, Pyrenomycetes, Xylariales, Amphisphaeriaceae.
26. Pestalotiopsis sp. Classification: Ascomycota, Pyrenomycetes, Xylariales, Amphisphaeriaceae.
27. *Poronia punctata*. Isolated from a sample collected in Sweden. Classification: Ascomycota, Pyrenomycetes, Xylariales, Xylariaceae.
28. Xylaria sp. Isolated from a leaf of the palm, *Sabal jamaicensis*, growing in Mona, Jamaica. Classification: Ascomycota, Pyrenomycetes, Xylariales, Xylariaceae Xylariaceae.
29. Nodulisporium sp. Classification: Ascomycota, Pyrenomycetes, Xylariales, Xylariaceae.
30. *Fusarium solani*. Isolated from a sample of grain of maize collected in India. Classification: Ascomycota, Pyrenomycetes, Hypocreales, Hypocreaceae.
31. Verticillium sp. A strain of Verticillium sp. has been deposited according to the Budapest Treaty on the International Recognition of the Deposits of Microorganisms for the Purpose of Patent Procedures, on Jan. 2, 1996, at Centraalbureau voor Schimmelcultures (CBS), under Accession No. CBS 830.95. Classification: Ascomycota, Pyrenomycetes, Hypocreales, Hypocreaceae.
32. *Volutella buxi*. Acc No of Strain: IMI 049467. Classification: Ascomycota, Pyrenomycetes, Hypocreales, Hypocreaceae.
33. *Chaetapiospora rhododendri*. Classification: Ascomycota, Pyrenomycetes, Xylariales, Xylariaceae, Hyponectriaceae.
34. *Lulworthia uniseptata*. A strain of *Lulworthia uniseptata* has been deposited according to the Budapest Treaty on the International Recognition of the Deposits of Microorganisms for the Purpose of Patent Procedures, on Jan. 28, 1997, at Centraalbureau voor Schimmelcultures (CBS), under Accession No. CBS 442.97. Classification: Ascomycota, Pyrenomycetes, Halosphaeriales, Halosphaeriaceae.
35. *Colletotrichum aculatum*. Classification: Ascomycota, Pyrenomycetes, Phyllachorales, Phyllachoraceae.
36. *Colletotrichum crassipes*. Classification: Ascomycota, Pyrenomycetes, Phyllachorales, Phyllachoraceae.
37. Cytospora sp. A strain of Cytospora sp has been deposited according to the Budapest Treaty on the International Recognition of the Deposits of Microorganisms for the Purpose of Patent Procedures, on Jan. 23, 1997, at Centraalbureau voor Schimmelcultures (CBS), under Accession No. CBS 424.97. Classification: Ascomycota, Pyrenomycetes, Diaporthales, Valsaceae.
38. Cytospora sp. A strain of Cytospora sp has been deposited according to the Budapest Treaty on the International Recognition of the Deposits of Microorganisms for the Purpose of Patent Procedures, on Jan. 23, 1997, at Centraalbureau voor Schimmelcultures (CBS), under Accession No. CBS 425.97. Classification: Ascomycota, Pyrenomycetes, Diaporthales, Valsaceae.
39. Discula sp. Classification: Ascomycota, Pyrenomycetes, Diaporthales, Valsaceae.
40. *Phomopsis ilicis*. Classification: Ascomycota, Pyrenomycetes, Diaporthales, Valsaceae.
41. *Phomopsis cirsii*. Classification: Ascomycota, Pyrenomycetes, Diaporthales, Valsaceae.
42. *Coryneum castaneicola*. Classification: Ascomycota, Pyrenomycetes, Diaporthales, Melanconidaceae.
43. *Seimatosporium lichenicola*. Classification: Ascomycota, Pyrenomycetes, Diaporthales, Melanconidaceae.
44. *Aspergillus tamarii*. Ex of Acc No of strain: CBS 821.72. Classification: Ascomycota, Plectomycetes, Eurotiales, Trichocomataceae.
45. *Eurotium chevalieri*. Ex of Acc No of strain: CBS 472.91. Classification: Ascomycota, Plectomycetes, Eurotiales, Trichocomataceae.
46. *Penicillium capsulatum*. Ex of Acc No of strain: CBS 273.86. Classification: Ascomycota, Plectomycetes, Eurotiales, Trichocomataceae.

47. *Penicillium olsonii.* Ex of Acc No of strain: CBS 523.89. Classification: Ascomycota, Plectomycetes, Eurotiales, Trichocomataceae.
48. *Penicillium pinophilum.* Ex of Acc No of strain: CBS 440.89. Classification: Ascomycota, Plectomycetes, Eurotiales, Trichocomataceae.
49. *Penicillium roqueforti.* Ex of Acc No of strain: CBS 167.91. Classification: Ascomycota, Plectomycetes, Eurotiales, Trichocomataceae.
50. *Penicillium italicum.* Ex of Acc No of strain: IMI 078 681. Classification: Ascomycota, Plectomycetes, Eurotiales, Trichocomataceae.
51. *Penicillium canescens.* Ex of Acc No of strain: CBS 579.70. Isolated from a salt mine in Egypt. Classification: Ascomycota, Plectomycetes, Eurotiales, Trichocomataceae.
52. *Eupenicillium javanicum.* Ex of Acc No of the strain: CBS 448.74. Classification: Ascomycota, Plectomycetes, Eurotiales, Trichocomataceae.
53. *Penicillium verruculosum.* Ex of Acc No of strain: CBS 563.92. Classification: Ascomycota, Plectomycetes, Eurotiales, Trichocomataceae.
54. *Talaromyces flavus.* Acc No of the strain: ATCC 52201. Classification: Ascomycota, Plectomycetes, Eurotiales, Trichocomataceae.
55. *Petromyces alliaceus.* Acc No of strain: CBS 511.69. Classification: Ascomycota, Plectomycetes, Eurotiales, Trichocomataceae.
56. *Trametes hirsuta.* Isolated from a sample collected in Denmark. Classification: Basidiomycota, Hymenomycetes, Coriolales, Coriolaceae.
57. Schizophyllum sp. A strain of Schizophyllum sp has been deposited according to the Budapest Treaty on the International Recognition of the Deposits of Microorganisms for the Purpose of Patent Procedures, on Jan. 28, 1997, at Centraalbureau voor Schimmelcultures (CBS), under Accession No. CBS 443.97. Classification: Basidiomycota, Hymenomycetes, Schizophyllales, Schizophyllaceae.
58. *Corticium roseum.* Isolated from a sample collected in Denmark. Classification: Basidiomycota, Hymenomycetes, Aleurodiscales Cortiaceae.
59. *Tubulicrinis subulatus.* Isolated from a sample collected in Denmark. Classification: Basidiomycota, Hymenomycetes, Xenasmatales, Tubulicrinaceae.
60. *Stereum hirsutum.* Isolated from a sample collected in Denmark. Classification: Basidiomycota, Hymenomycetes, Stereales, Stereaceae.
61. Strains of the Classification: *Mitosporic fungus: Acrodontium crateriforme, Aureobasidium pullulans,* Circinotrichum sp., Cryptocline sp., Ellisiopsis sp., *Epicoccum nigrum,* Gliocladium sp., *Helicorhoidion irregulare,* Hendersonia sp., Mariannaea sp., Microsphaeropsis sp., Ramularia sp., Sarcopodium sp., Spadicoides sto. Acc No of strain IMI203428, *Speiropsis pedatospora, Sporotrichum exile.* Acc No of strain CBS 350.47, Stilbella sp., Trichothecium sp., *Trimmatostroma abietes, Tubakia dryina,* Wiesneriomyces sp., and *Zygosporium masonii.*
62. *Vialaea insculpta.* Classification: Uncertain.
63. *Bacillus alcalophilus.* A strain of *Bacillus alcalophilus* has been deposited according to the Budapest Treaty on the International Recognition of the Deposits of Microorganisms for the Purpose of Patent Procedures, on Feb. 12, 1997, at Deutsche Sammlung von Mikroorganismen und Zellkulturen GmbH, under Accession No. DSMZ 11404.

The taxonomic classification used herein builds primarily on the system used in the NIH Database (Entrez, version spring 1996) available on World Wide Web at http://www.ncbi.nlm.nih.gov/Taxonomy/tax.html.

Classification of organisms not included in the Entrez database may be found in the following reference books which are generally available and accepted in the art:

Ascomycetes: Eriksson, O. E. & Hawksworth, D. L.: Systema Ascomycetum vol 12 (1993);

Basidiomycetes: Jülich, W.: *Higher Taxa of Basidiomycetes, Bibliotheca Mycologia* 85, 485pp (1981);

Zygomycetes: O÷Donnell, K.: Zygomycetes in culture, University of Georgia, US, 257pp (1979). General mycological reference books include: Hawksworth, D. L., Kirk, P. M., Sutton, B. C. and Pegler, D. N. *Dictionary of the fungi,* International Mycological Institute, 616 pp (1995); and Von Arx, J. A. The genera of fungi sporulating in culture, 424 pp (1981).

The XET may be obtained from the organism in question by any suitable technique, and in particular by use of recombinant DNA techniques known in the art (c.f. Sambrook, J. et al., 1989, *Molecular Cloning, A Laboratory Manual,* Cold Spring Harbor Press, Cold Spring Harbor, N.Y., USA). The use of recombinant DNA techniques generally comprises cultivation of a host cell transformed with a recombinant DNA vector, consisting of the product gene of interest inserted between an appropriate promoter and terminator, in a culture medium under conditions permitting the expression of the enzyme and recovering the enzyme from the culture. The DNA sequence may be of genomic, cDNA or synthetic origin or any mixture of these, and may be isolated or synthesised in accordance with methods known in the art. The enzyme may also be obtained from its naturally occurring source, such as a plant or organism, or relevant part thereof.

When an XET is added to dough intended for use in the preparation of baked products, it may exert a strengthening effect on dough constituents. The XET is used in an amount sufficient to provide the desired effect, i.e., the improved properties in question. Thus, the dosage of the XET to be used in the methods of the present invention should be adapted to the nature and composition of the dough in question as well as to the nature of the XET to be used.

The term "composition" is defined herein as a dough-improving and/or baked product-improving composition which, in addition to the XET, comprises one or more additional substances conventionally used in baking. The additional substance(s) may be other enzymes or chemical additives known in the art to be useful in dough preparation and/or baking.

The bread-improving and/or dough improving composition of the invention is generally included in the dough in an amount corresponding to 0.01–5%, in particular 0.1–3%. The XET is typically added in an amount corresponding to 0.01–100 mg enzyme protein per kg of flour, preferably 0.1–25 mg enzyme protein per kg of flour, more preferably 0.1–10 mg enzyme protein per kg of flour, and most preferably 0.5–5 mg enzyme protein per kg of flour, particularly 1–5 mg/kg.

In terms of enzyme activity, the appropriate dosage of a given XET for exerting a desirable improvement of dough and/or baked products will depend on the enzyme and the enzyme substrate in question. The skilled person may determine a suitable enzyme unit dosage on the basis of methods known in the art.

In a preferred embodiment, the dough-improving and/or baked product-improving composition of the invention comprises an XET selected from the group consisting of:

(a) a polypeptide which is encoded by a nucleic acid sequence which hybridizes under low stringency conditions with (i) the nucleic acid sequence set forth in SEQ ID NO:1, (ii) its complementary strand, or (iii) a subsequence thereof;

(b) a polypeptide having an amino acid sequence which has at least 50% identity with the amino acid sequence set forth in SEQ ID NO:2;

(c) an allelic variant of (a) or (b); and (d) a fragment of (a), (b) or (c), wherein the fragment retains XET activity.

Hybridisation indicates that by methods of standard Southern blotting procedures (for example, as described by J. Sambrook, E. F. Fritsch, and T. Maniatus (1989, *Molecular Cloning, A Laboratory Manual*, 2d edition, Cold Spring Harbor, N.Y.), the nucleic acid sequence hybridizes to an oligonucleotide probe corresponding to the polypeptide encoding part of the nucleic acid sequence shown in SEQ ID NO:1, under low to high stringency conditions (i.e., prehybridization and hybridization at 42° C. in 5X SSPE, 0.3% SDS, 200 µg/ml sheared and denatured salmon sperm DNA, and either 25, 35 or 50% formamide for low, medium and high stringencies, respectively). In order to identify a clone or DNA which is homologous with SEQ ID NO:1, the hybridisation reaction is washed three times for 30 minutes each using 2×SSC, 0.2% SDS preferably at least 50° C., more preferably at least 55° C., more preferably at least 60° C., more preferably at least 65° C., even more preferably at least 70° C., and most preferably at least 75° C.

The aforementioned probe can be considerably shorter than the entire sequence, but should be at least 15, preferably at least 25, and more preferably at least 40 nucleotides in length. Longer probes can also be used. Both DNA and RNA probes can be used. The probes are typically labelled for detecting the corresponding gene (for example, with $^{32}P$, $^{3}H$, $^{35}S$, biotin, or avidin). For example, molecules to which a $^{32}P$-, $^{3}H$- or $^{35}S$-labelled oligonucleotide probe hybridizes may be detected by use of X-ray film.

The aforementioned polypeptide has an amino acid sequence which has a degree of identity to the amino acid sequence of SEQ ID NO:2 of at least about 50%, preferably at least about 60%, preferably at least about 70%, more preferably at least about 80%, even more preferably at least about 90%, most preferably at least about 95%, and even most preferably at least about 97%, which retain XET activity ) (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from the amino acid sequence of SEQ ID NO:2. For purposes of the present invention, the degree of identity between two amino acid sequences may be suitably determined by means of computer programs known in the art, such as GAP provided in the GCG program package (Program Manual for the Wisconsin Package, Version Aug. 8, 1994, Genetics Computer Group, 575 Science Drive, Madison, Wis., USA 53711) (Needleman, S. B. and Wunsch, C. D., (1970), Journal of Molecular Biology, 48, 443–453, using GAP with the following settings for polypeptide sequence comparison: GAP creation penalty of 3.0 and GAP extension penalty of 0.1.

An allelic variant denotes any of two or more alternative forms of a gene occupying the same chomosomal locus. Allelic variation arises naturally through mutation, and may result in phenotypic polymorphism within populations. Gene mutations can be silent (no change in the encoded polypeptide) or may encode polypeptides having altered amino acid sequences. The term allelic variant is also used to denote a protein encoded by an allelic variant of a gene.

The XET and/or additional enzymes to be used in the methods of the present invention may be in any form suited for the use in question, e.g., in the form of a dry powder, agglomerated powder, or granulate, in particular a non-dusting granulate, a liquid, in particular a stabilized liquid, or a protected enzyme. Granulates and agglomerated powders may be prepared by conventional methods, e.g., by spraying the XET onto a carrier in a fluid-bed granulator. The carrier may consist of particulate cores having a suitable particle size. The carrier may be soluble or insoluble, e.g., a salt (such as NaCl or sodium sulfate), a sugar (such as sucrose or lactose), a sugar alcohol (such as sorbitol), starch, rice, corn grits, or soy. The XET and/or additional enzymes may be contained in slow-release formulations. Methods for preparing slow-release formulations are well known in the art. Liquid enzyme preparations may, for instance, be stabilized by adding nutritionally acceptable stabilizers such as a sugar, a sugar alcohol or another polyol, lactic acid, or another organic acid according to established methods. Granulated enzymes may be prepared according to the method disclosed in WO 97/423839.

For inclusion in pre-mixes or flour it is advantageous that the XET is in the form of a dry product, e.g., a non-dusting granulate, whereas for inclusion together with a liquid it is advantageously in a liquid form.

A substrate of the XET in question may also be incorporated into the dough. The substrate may be incorporated into dough separately or together with the XET of interest, optionally as constituent(s) of the bread-improving and/or dough-improving composition. Alternatively, an enzyme which acts on a substance endogenous to the flour to produce a substrate for the XET of interest may also be incorporated in the dough.

The specific amount of the substrate available for the XET of interest will depend on a number of factors, such as the baking process used, the length of time for mixing, fermentation, proofing and/or baking, the quality of the yeast and/or flour used, as well as the activity of endogenous and exogenous enzymes present.

A preferred substrate for XET is xyloglucan.

One or more additional enzymes may also be incorporated into the dough. The additional enzyme may be of any origin, including mammalian and plant, and preferably of microbial (bacterial, yeast or fungal) origin and may be obtained by techniques conventionally used in the art.

In a preferred embodiment, the additional enzyme may be an amylase, such as an alpha-amylase (useful for providing sugars fermentable by yeast and retarding staling), a beta-amylase, a cyclodextrin glucanotransferase, a peptidase, in particular, an exopeptidase (useful in flavour enhancement), a translutaminase, a lipase (useful for the modification of lipids present in the dough or dough constituents so as to soften the dough), a phospholipase (useful for the modification of lipids present in the dough or dough constituents so as to soften the dough and improving gas retention in the dough), a cellulase, a hemicellulase, in particular a pentosanase such as xylanase (useful for the partial hydrolysis of pentosans which increases the extensibility of the dough), a protease (useful for gluten weakening in particular when using hard wheat flour), a protein disulfide isomerase, e.g., a protein disulfide isomerase as disclosed in WO 95/00636, a glycosyltransferase, and an oxidoreductase, e.g., a dehydrogenase, a cellobiose dehydrogenase, a fructose dehydrogenase or a lactate dehydrogenase; a peroxidase (useful for improving the dough consistency), a laccase, an aldose oxidase, a glucose oxidase, a pyranose oxidase, a lipoxygenase, an L-amino acid oxidase (useful in improving dough consistency) or a carbohydrate oxidase.

Commercially available amylases useful in the present invention are NOVAMYL™ (a *Bacillus stearothermophilus* maltogenic amylase, available from Novo Nordisk A/S, Denmark), FUNGAMYL® (an *Aspergillus oryzae* alpha-amylase, available from Novo Nordisk A/S, Denmark), and BAN™ (a *Bacillus licheniformis* alpha-amylase, available from Novo Nordisk A/S, Denmark). A commercially available amyloglucosidase useful in the present invention is AMG™ (an *Aspergillus niger* amyloglucosidase, available from Novo Nordisk A/S, Denmark). Other useful commercially available amylase products include GRIND-AMYLTM™ A 1000 or A 5000 (available from Grindsted Products, Denmark) and AMYLASE H or AMYLASE P (available from Gist-Brocades, The Netherlands). A commercially available glucose oxidase useful in the present invention is GLUZYME™ (an *Aspergillus niger* glucose oxidase, available from Novo Nordisk A/S, Denmark). Commercially available proteases useful in the present invention are NEUTRASE™ (a *Bacillus amyloliquefaciehs* endoprotease, available from Novo Nordisk A/S, Denmark) and GLUTENASE™ (available from Novo Nordisk A/S, Denmark). A commercially available pentosanase useful in the present invention is PENTOPAN™ (a *Humicola insolens* pentosanase, available from Novo Nordisk A/S, Denmark). A commercially available lipase useful in the present invention is NOVOZYM® 677 BG (a *Thermomyces lanuginosus* lipase, available from Novo Nordisk A/S, Denmark).

When one or more additional enzyme activities are to be added in accordance with the methods of the present invention, these activities may be added separately or together with the XET, optionally as constituent(s) of the bread-improving and/or dough-improving composition. The other enzyme activities may be any of the above described enzymes and may be dosed in accordance with established baking practice.

In addition to the above mentioned additional enzymes, the XET may contain varying minor amounts of other enzymatic activities inherently produced by the producer organism in question.

In addition, or as an alternative, to additional enzyme components, one or more conventionally used dough and/or bread improving agents may also be incorporated into the dough. The agent may include proteins, such as milk powder (to provide crust colour), gluten (to improve the gas retention power of weak flours), and soy (to provide additional nutrients and improve water binding); eggs such (either whole eggs, egg yolks or egg whites); fat such as granulated fat or shortening (to soften the dough and improve the texture of the bread); an emulsifier (to improve dough extensibility and, to some extent, the consistency of the resulting bread); an oxidant, e.g., ascorbic acid, potassium bromate, potassium iodate, azodicarbon amide (ADA) or ammonium persulfate (to strengthen the gluten structure); an amino acid, e.g., L-cysteine (to improve mixing properties); a sugar; a salt, e.g., sodium chloride, calcium acetate, sodium sulfate or calcium sulphate (to make the dough firmer); flour; and starch. Such components may also be added to the dough in accordance with the methods of the present invention.

Examples of suitable emulsifiers are mono- or diglycerides, diacetyl tartaric acid esters of mono- or diglycerides, sugar esters of fatty acids, polyglycerol esters of fatty acids, lactic acid esters of monoglycerides, acetic acid esters of monoglycerides, polyoxyethylene stearates, phospholipids, lysolecithin and lecithin.

The dough and/or baked product prepared by a method of the present invention may be based on wheat meal or flour, optionally in combination with other types of meal or flour such as corn meal, corn flour, rye meal, rye flour, oat meal. oat flour, soy meal, soy flour, sorghum meal, sorghum flour, potato meal, or potato flour.

The handling of the dough and/or baking may be performed in any suitable manner for the dough and/or baked product in question, typically including the steps of kneading the dough, subjecting the dough to one or more proofing treatments, and baking the product under suitable conditions, i.e., at a suitable temperature and for a sufficient period of time. For instance, the dough may be prepared by using a normal straight dough process, a sour dough process, an overnight dough method, a low-temperature and long-time fermentation method, a frozen dough method, the Chorleywood Bread process, or the Sponge and Dough process.

From the above disclosure it will be apparent that the dough of the invention is generally a leavened dough or a dough to be subjected to leavening. The dough may be leavened in various ways such as by adding sodium bicarbonate or the like, or by adding a leaven (fermenting dough), but it is preferable that the dough be leavened by adding a suitable yeast culture, such as a culture of *Saccharomyces cerevisiae* (baker's yeast). Any of the commercially available *Saccharomyces cerevisiae* strains may be employed.

The present invention also relates to the use of an XET for the preparation of pasta dough, preferably prepared from durum flour or a flour of comparable quality. The dough may be prepared by use of conventional techniques and the XET used in a similar dosage as that described above. The XET may be any of the types described above. When used in the preparation of pasta, the XET results in a strengthening of the gluten structure, a reduction in the dough stickiness, and an increased dough strength.

The present invention also relates to methods for preparing a baked product, comprising baking a dough produced by a method of the present invention to produce a baked product. The baking of the dough to produce a baked product may be performed using methods well known in the art.

The present invention also relates to dough and/or bread improving compositions comprising an effective amount of an XET for improving one or more properties of a dough and/or a baked product obtained from the dough, and a carrier and/or a baking ingredient. The compositions may further comprise a substrate for the XET, one or more additional enzymes, one or more conventionally used dough and/or bread improving agents, an enzyme which acts on a substance endogenous to the flour to produce a substrate for the XET, and/or a substance and the enzyme which acts on the substance to produce a substrate for the XET.

The present invention also relates to doughs and baked products, respectively, produced by the methods of the present invention.

The present invention further relates to a pre-mix, e.g., in the form of a flour composition, for dough and/or baked products made from dough, in which the pre-mix comprises an XET. The term "pre-mix" is defined herein to be understood in its conventional meaning, i.e., as a mix of baking agents, generally including flour, which may be used not only in industrial bread-baking plants/facilities, but also in retail bakeries. The pre-mix may be prepared by mixing an XET or a bread-improving and/or dough-improving composition of the invention comprising an XET with a suitable carrier such as flour, starch, a sugar or a salt. The pre-mix may contain other dough-improving and/or bread-improving additives, e.g., any of the agents, including enzymes, mentioned above.

The present invention further relates to baking additives in the form of a granulate or agglomerated powder, which comprises the XET. The baking additive preferably has a narrow particle size distribution with more than 95% (by weight) of the particles in the range from 25 to 500 μm.

The present invention is further described by the following examples which should not be construed as limiting the scope of the invention.

EXAMPLES

Materials and Methods

Preparation of White Bread (I)

The straight-dough bread-making method may be used according to AACC Method 10–10B (in Approved Methods of the American Association of Cereal Chemists, Ninth Edition, March 1995; AACC, St. Paul Minn., USA).

| Basic recipe | |
|---|---|
| Wheat flour | 100% |
| Salt | 1.5% |
| Yeast (fresh) | 5.3% |
| Sugar | 6.0% |
| Shortening | 3.0% |

Water determined empirically

All percentages are by weight relative to the wheat flour.
Procedure
1. Dough mixing (Hobart mixer):
   The mixing time and speed should be determined by the skilled baker so as to obtain an optimum dough consistency under the testing conditions used.
2. 1st punch (e.g., 52 minutes after start)
3. 2nd punch (e.g., 25 minutes later)
4. Moulding and panning (e.g., 13 minutes later).
5. Proofing to desired height (e.g., 33 minutes at 32° C., 82% RH)
5. Baking (e.g., at 215° C. for 24 minutes)

Preparation of White Bread (II)

The sponge-dough bread-making method may be used according to AACC Method 10–11 (in Approved Methods of the American Association of Cereal Chemists, Ninth Edition, March 1995; ACC, St. Paul Minn., USA).

| Basic recipe for Sponge | |
|---|---|
| Wheat flour | 60% |
| Yeast (compressed) | 36% |
| Yeast Food | 2% |
| Water | 36% |

All percentages are by weight relative to the wheat flour.
Procedure
1. Add water to compressed yeast
2. Add yeast food in dry form with flour
3. Mix sponge (Hobart A-120; Hobart Corp., Troy Ohio, USA):
   0.5 minute at $1^{st}$ speed
   1 minute at $2^{nd}$ speed
   The mixing time may be adjusted so as to obtain an optimum dough consistency under the testing conditions used.
4. Ferment in a fermentation cabinet: 4 hours at 30° C., 85% RH

| Basic recipe for Dough | |
|---|---|
| Wheat flour | 40% |
| Water | 24% |
| Sugar | 5% |
| Shortening | 3% |
| Salt | 2% |

All percentages are by weight relative to the wheat flour.
Procedure
1. Add dough ingredients; begin mixer ($1^{st}$ speed)
2. Add sponge in three approximately equal portions at 15, 25, and 35 seconds mixing time; total mixing time: 1 minute
3. At $2^{nd}$ speed, mix to obtain an optimum dough consistency
4. Ferment in a fermentation cabinet: 30 minutes at 30° C., 85% RH
5. Intermediate proof: 12–15 minutes in fermentation cabinet
6. Mould and final proof at 35.5° C., 92% relative humidity
7. Bake: 25 minutes at 218° C.

Evaluation of Staling Properties of Bread

The degree of staling is determined on bread, e.g., on day 1, 3, 7 and 9 after baking. Evaluation of staleness and texture can be done according to AACC method 74-09. The principles for determination of softness and elasticity of bread crumb are as follows:
1. A slice of bread is compressed with a constant speed in a texture analyser, measuring the force for compression in g.
2. The softness of the crumb is measured as the force at 25% compression.
3. The force at 40% compression (P2) and after keeping 40% compression constant for 30 seconds (P3) is measured. The ratio (P3/P2) is the elasticity of the crumb.

Preparation of White Layer Cake

The method may be used according to AACC Method 10-90 (in Approved Methods of the American Association of Cereal Chemists, Ninth Edition, March 1995; AACC, St. Paul Minn., USA).

| Basic recipe | |
|---|---|
| Flour | 100% |
| Sugar | 140% |
| Shortening | 50% |
| Non-fat Dry Milk | 12% |
| Dried Egg Whites | 9% |
| Salt | 3% |

Baking Powder, Water determined empirically

All percentages are by weight relative to the flour.
Procedure
1. Combine all dry ingredients and sift well
2. Add shortening and 60% of water
3. Mix at low speed for 0.5 minute in Hobart C-100 mixer
4. Mix at medium speed for 4 minutes
5. Add 50% of remaining water
6. Mix at low speed for 0.5 minute, scrape down and mix at medium speed for 2 minutes
7. Add remaining water, mix at low speed for 0.5 minute, scrape down and mix at medium speed for 2 minutes
8. Scale batter into each of two greased pans
9. Bake at 175–190° C.

Evaluation of Cakes

Cakes should be graded for volume and texture on the same day as baked according to AACC Method 10–90.

The internal structure may be scored for the uniformity and size of cells as well as thickness of the walls; the grain; texture, such as moisture, tenderness and softness; crumb colour; and flavour.

Preparation of Cookies

Cookies may be prepared according to AACC Method 10–50D (in Approved Methods of the American Association of Cereal Chemists, Ninth Edition, March 1995; AACC, St. Paul Minn., USA).

| Basic recipe | |
|---|---|
| Flour | 225 g |
| Water | 16 g |
| Dextrose Solution | 33 g |
| Bicarbonate of Soda | 2.5 g |
| Salt | 2.1 g |
| Sugar | 130 g |
| Shortening | 64 g |

Procedure
1. Cream shortening, sugar, salt and soda on low speed 3 minutes using an electric mixer (e.g., Hobart C-100)
2. Add dextrose solution and distilled water
3. Mix at low speed for 1 minute
4. Mix at medium speed for 1 minute
5. Add all flour and mix at low speed for 2 minutes
6. Scrape dough from bowl and place six portions at well-spaced points on lightly greased cookie sheet
7. Flatten dough lightly
8. Cut dough with cookie cutter
9. Bake at 205° C. for 10 minutes Evaluation of Cookies Cookie width should be measured after cooling 30 minutes and can be done by the method according to AACC Method 10–50D.

The width of each of the six cookies is measured in mm, then rotated 90° and remeasured to obtain the average width (W). An average thickness (T) may be obtained by measuring the cookies stacked on top of one another, then restacked in a different order. The spread factor is the ratio of W/T. However, the most sensitive and reliable estimate is the width measurement, and in some cases, thickness. Because the spread factor is a ratio of 2 empirically determined parameters, different values of W and T can result in the same W/T.

Preparation of Biscuits

Biscuits may be prepared according to AACC Method 10-31B (in Approved Methods of the American Association of Cereal Chemists, Ninth Edition, March 1995; AACC, St. Paul Minn., USA).

| Basic recipe | |
|---|---|
| Flour | 228 g |
| Shortening | 40 g |
| Milk Solution[1] | 135 g |
| Bicarbonate of Soda[2] | 3.4 g |
| Salt[2] | 4.5 g |
| Monocalcium Phosphate[2] | 130 g |

[1]50 g milk powder in 450 ml water
[2]omit if self-rising flour is used; use 240 g of self-rising flour Procedure
1. Sift together flour and other dry ingredients (bicarbonate of soda, salt and monocalcium phosphate, if used)
2. Add shortening to flour mixture
3. Mix, using electric mixer (e.g., Hobart, Kitchen Aid or equivalent) with timer control, at speed 1 for 15 seconds
4. Mix at speed 1 for 3 minutes
5. Add milk solution and mix at speed 1 for 15 seconds
6. Roll out dough using floured rolling pin
7. Cut dough with floured cutter
8. Place 8 dough pieces 4 cm apart on ungreased baking sheet.
9. Bake at 232° C. for 10 minutes Evaluation of Biscuits Upon removal from oven, biscuits should be removed from the baking sheet and cooled for 30 minutes. Measurements of the eight biscuits can be made according to AACC Method 10–31B to obtain a total weight, a total diameter and a height at the top centre of each biscuit.

Preparation of Pie Shells

Pie shells may be prepared according to AACC Method 10-60 (in Approved Methods of the American Association of Cereal Chemists, Ninth Edition, March 1995; AACC, St. Paul Minn., USA).

| Basic recipe | |
|---|---|
| Flour | 100% |
| Shortening | 60% |
| Salt | 3.5% |
| Water | 30–64% |

All percentages are by weight relative to the wheat flour, and all ingredients are at 10° C. before mixing.
Dough Preparation
1. Sift flour twice
2. Add shortening to flour and cut for 5 minutes using electric mixer (e.g., Hobart, Kitchen Aid or equivalent) with timer control, on low speed
3. Dissolve salt in a portion of water
4. Add salt solution to flour-shortening mixture, together with additional water if necessary
5. Mix at low speed for 2 minutes
6. Store dough at 10° C. for 24 hours Empty shells
1. Scale, press dough into ball
2. Roll dough, fold and roll again
3. Fold and roll a third time
4. Lay dough sheet over an inverted pie tin
5. Trim dough and prick with fork
6. Let dry for 30 minutes and cover with a second pan pressed down firmly
7. Bake at 218° C. for 20–25 minutes, removing second pan after 10 minutes in the oven Filled pies
1. Scale and roll bottom crust as outlined above for empty pie shell
2. Press dough sheet into pie tin and fill with either artificial fruit acid filling (water, corn starch, sugar and citric acid crystals) or true fruit filling (cling peaches, sugar corn starch and water)
3. Scale and roll dough once for top crust
4. Place over filling, trim and cut centre lightly
5. Press edge over wetted edge of bottom crust
6. Bake at 218° C. for about 30 minutes.

Evaluation of Pie Crusts

Viscosity may be evaluated according to AACC Method 56-80. Other parameters of empty and filled pie shells may be measured according to AACC Method 10-60 24 hours and 12 or 16 hours after baking, respectively. Pie crusts may be evaluated empirically for whether they are baked through; the edges have shrunk from edge of pan; blisters have appeared; the texture is flaky; the mouth-feel is tender; whether they are crisp or soft; the colour; and if the fruit filling has penetrated the crust.

Testing of Doughs and Breads

According to the methods of the present invention, the effect of adding an XET may be tested in doughs and breads by using the following method:

| Recipe: | |
|---|---|
| Water | 60% |
| Wheat Flour | 100% |
| Yeast | 4% |
| Salt | 1.5% |
| Sugar | 1.5% |

Procedure for Preparation of Breads
1. Dough mixing (Spiral mixer)
   3 minutes at low speed
   8 minutes at high speed
   The mixing time may be adjusted by the skilled baker to obtain an optimum dough consistency under the testing conditions used.
2. 1st proof: 30° C.—80% RH, 20 minutes
3. Scaling and shaping;
4. Final proof: 32° C.—80% RH, 40 minutes;
5. Baking: 225° C., 20 minutes for rolls and 30 minutes for loaf.

Evaluation of Dough and Baked Products

Dough and baked products made from the straight dough method described above may be evaluated as follows for loaf specific volume, dough stickiness, dough firmness, dough extensibility, dough elasticity, crumb structure, and gluten strength.

Loaf specific volume: The mean value of 4 loaves volume is measured using the traditional rapeseed displacement method. The specific volume is calculated as volume per weight of bread (ml/g). The specific volume of the control (without enzyme) is defined as 100. The relative specific volume index is calculated as follows:

$$\text{Specific vol. index} = \frac{\text{specific vol. of 4 loaves}}{\text{spec. vol. of 4 control loaves}} \times 100$$

The dough stickiness, firmness, extensibility, elasticity and crumb structure may be evaluated relative to controls by the skilled test baker according to the following scales:

| | 1 | 2 | 3 | 4 | 5 | 6 |
|---|---|---|---|---|---|---|
| Dough Stickiness | almost liquid | too sticky | sticky | normal | dry | not used |
| Crumb Structure | very poor | poor | non-uniform | uniform/ good | very good | not used |
| Dough Firmness | extremely soft | too soft | soft/ good | normal | firm | too firm |
| Dough Extensibility | too short | short | normal | good | long | too long |

Dough stability/Shock test: After the second proof a pan containing the dough is dropped from a height of 20 cm. The dough is baked and the volume of the resulting bread is determined.

Gluten Strengthening: The strengthening effect of a given dough conditioner on wheat flour dough or gluten dough may be measured by dynamic rheological measurements. These measurements are able to show the strength of a dough under oscillation. Both wheat flour dough and gluten dough are viscoelastic materials. In oscillatory measurements, the viscoelastic properties of a wheat dough and a gluten dough can be divided into two components, the dynamic shear storage modulus G' and the dynamic shear loss modulus G". The ratio of the loss and the storage moduli is numerically equal to the tangent of the viscoelastic phase angle δ (Delta). An increase in the storage modulus G' and a decrease in the phase angle δ indicate a stronger and more elastic dough.

Example 1

Cloning and Expression of an XET from
*Tiarosporella phaseolina* CBS No. 446.97

Chemicals used as buffers and substrates were commercial products of at least reagent grade.

Deposited organism:
*Tiarosporella phaseolina* CBS No. 446.97
Other strains:
W3124: a *Saccharomyces cerevisiae* strain (MATa; ura 3-52; leu 2-3, 112; his 3-D200; pep 4-1137; prc1::HIS3; prb1::LEU2; cir+) as described by van den Hazel, H. B; Kielland-Brandt, M. C.; Winther, J. R. Eur. *J. Biochem.* 207: 277–283, 1992.
DH10B: an *E. coli* strain (Life Technologies, Rockville Md., USA)
Plasmids:
pHD414: an Aspergillus expression vector derived from the plasmid p775 (EP 238 023) and described in WO 93/11249
pYES 2.0: (Invitrogen, San Diego Calif., USA)
p3SR2: an *Aspergillus niger* plasmid containing the amdS gene (Christiensen, T., et al., 1988. Bio/Technology 6: 1419–22)

Media:

YPD: 10 g yeast extract, 20 g peptone, $H_2O$ to 900 ml; autoclaved; 100 ml 20% glucose (sterile filtered) added YPM: 10 g yeast extract, 20 g peptone, $H_2O$ to 900 ml; autoclaved; 100 ml 20% maltodextrin (sterile filtered) added SC-URA: 100 ml 10x Basal salt (75 g yeast nitrogen base, 113 g succinic acid, 68 g NaOH, $H_2O$ ad 1000 ml, sterile filtered), 28 ml 20% casamino acids without vitamins, 10 ml 1% tryptophan, $H_2O$ ad 900 ml, autoclaved, 3.6 ml 5% threonine and 100 ml 20% glucose or 20% galactose added SC-agar:SC-URA; 20 g/l agar added Molecular Biology Methods Expression cloning in yeast, extraction of RNA, cDNA synthesis, mung bean nuclease treatment, blunt-end formation with T4 DNA polymerase, and construction of libraries were performed as described by H. Dalboege et al. (1994, Mol. Gen. Genet. 243: 253–260.; WO 93/11249; WO 94/14953, which are hereby incorporated by reference).

Assay for XET Activity

The assay uses an "XET-paper," a xyloglucan-coated paper which is dipped in a solution of labelled oligosaccharide, which is described in WO 97/11193. The procedure includes a method for preparing a labelled oligosaccharide and preparing xyloglucan-coated paper.

Preparation of labelled oligosaccharide

One gram of the reducing oligosaccharide 4-O-[4-O-[4-O-[6-O-α-D-xylopyranosyl-β-D-glucopyranosyl]-6-O-(2-O-β-D-galactopyranosyl)-α-D-xylopyranosyl-β-D-glucopyranosyl]-6-0-(2-O-β-D-galactopyranosyl)-α-D-xylopyranosyl-β-D-glucopyranosyl]-D-glucose ("XLLG") is dissolved in 25 ml of a saturated aqueous solution of ammonium hydrogencarbonate containing 1 gram of sodium cyanoborohydride ($NaCNBH_3$) and incubated in the dark at 25° C. for 7 days to permit reductive amination. The ammonium hydrogencarbonate is then removed by evaporation, and the (ninhydrin-reactive) aminated derivative of XLLG is purified, e.g., by gel-permeation chromatography or cation-exchange chromatography. The product is believed to be an oligosaccharidyl-1-amino-1-deoxyalditol, i.e., a derivative of XLLG in which the reducing terminal D-glucose moiety has been replaced by 1-amino-1-deoxy-D-glucitol.

Fifty mg of oligosaccharidyl-1-amino-1-deoxyalditol is dissolved in 3 ml of 3% borax (disodium tetraborate; pH 9.0–9.5) and a freshly prepared solution of 10 mg lissamine rhodamine sulphonyl chloride (LSRSC) (Molecular Probes Inc., Eugene Oreg., USA) in 0.75 ml of dry dimethylformamide (DMF) is added gradually, with stirring, and the mixture is incubated in the dark overnight. An additional 0.75 ml of LSRSC-DMF solution is added and the mixture incubated for eight hours. The bright pink oligosaccharidyl-1-amino-1-deoxyalditol-lissamine-rhodamine conjugate (XLLGol-SR) is purified by gel-permeation chromatography followed by reversed-phase chromatography on a $C_{18}$-silica gel column. After the column is washed with water, a methanol gradient is applied; the XLLGol-SR elutes in about 50% methanol.

Preparation of Xyloglucan-impregnated Paper

Whatman No.1 filter paper is moistened with a 1% aqueous solution of xyloglucan and dried. The XLLGol-SR preparation is diluted in 75% aqueous acetone to give an absorbance at 580 nm ($A_{580}$) of 0.2. The xyloglucan-coated paper is then dipped in the XLLGol-SR solution and re-dried, resulting in "XET-paper".

Assay Procedure

An aliquot of the solution to be tested for XET activity is spotted onto XET-paper. Before the test sample dries, the sheet is quickly sandwiched between two sheets of plastic (e.g., clear acetate sheets) and incubated, e.g., at 20° C. for 1 hour. The incubated XET-paper with the plastic backing is then placed (paper-side down) in a dish containing about 150 ml of a solvent, e.g., freshly prepared ethanol/formic acid/water (1:1:1 by volume) which removes from the paper any unreacted XLLGol-SR but not XLLGol-SR which has become incorporated into the xyloglucan. The XET-paper is then rinsed in running water for 5 minutes, then washed in approximately 100 ml of acetone for 5 minutes, and dried thoroughly. The paper is then examined under a short-wavelength ultraviolet lamp (e.g., emitting at 254 nm). The presence of XET is seen as a pink (orange-fluorescing) spot, which can be quantified, e.g., by use of a scanning spectrofluorometer.

Culture Cultivation

*Tiarosporella phaseolina* CBS No. 446.97 was inoculated from a plate with outgrown mycelium into a shake flask containing 100 ml medium B (20 g soyabean meal, 5 g maltodex 01, (Roquette 101-7845), 15 g wheat bran, 3 g peptone (Difco 0118), 10 g cellulose avicel (Merck 2331), 0.2 ml pluronic (PE-6100, 101-3068), 1 g olive oil, deionized water to 1000 ml). The culture was incubated at 26° C. and 200 rpm for 7 days. The resulting culture broth was filtered through miracloth and the mycelia were stored in liquid nitrogen.

RNA Isolation

Total RNA was extracted from frozen mycelia using guanidinium thiocyanate followed by ultracentrifugation through a 5.7 M CsCl cushion. Poly(A)+ RNA was purified by oligo(dT)-cellulose affinity chromatography using the procedures described in WO 94/14953.

cDNA Synthesis

Double-stranded cDNA was synthesised from 5 mg poly (A)+ RNA by the RNase H method (Gubler and Hoffman, 1983. Gene 25:263–269; Sambrook, J. et al., supra). The poly(A)+ RNA (5 μg in 5 μl of DEPC-treated water) was heated at 70° C. for 8 min. in a pre-siliconized, RNase-free microfuge tube, quenched in ice, then 45 μl of reverse transcriptase buffer (50 mM Tris-Cl, pH 8.3, 75 mM KCl, 3 mM $MgCl_2$, 10 mM DTT, Bethesda Research Laboratories) containing 1 mM dATP, dGTP and dTTP and 0.5 mM 5-methyl-dCTP (Pharmacia Biotech, Uppsala SE), 40 units human placental ribonuclease inhibitor (RNasin, Promega Corp., Madison Wis., USA), 1.45 pg of oligo(dT)$_{18}$-Not I primer (Pharmacia Biotech) and 1000 units SuperScript II RNase H reverse transcriptase (Bethesda Research Laboratories) was added. First-strand cDNA was synthesised by incubating the reaction mixture at 45° C. for 1 hour. After synthesis, the mRNA:cDNA hybrid mixture was filtered through a MicroSpin S-400 HR (Pharmacia Biotech) spin column according to the manufacturer's instructions.

The recovered hybrids were diluted in 250 μl second strand buffer (20 mM Tris-Cl, pH 7.4, 90 mM KCl, 4.6 mM $MgCl_2$, 10 mM $(NH_4)_2SO_4$, 0.16 mM bNAD+) containing 200 μl of each dNTP, 60 units *E. coli* DNA polymerase I (Pharmacia Biotech), 5.25 units RNase H (Promega Corp.) and 15 units *E. coli* DNA ligase (Boehringer Mannheim GmbH, Mannheim Del.). Second strand cDNA synthesis was achieved by incubating the reaction tube at 16° C. for 2 hours and an additional 15 min. at 25° C. The reaction was stopped by addition of EDTA to a final concentration of 20 mM followed by phenol and chloroform extractions.

Mung Bean Nuclease Treatment

The double-stranded cDNA was precipitated at −20° C. for 12 hours by addition of 2 vols 96% EtOH, 0.2 vol 10 M NH$_4$Ac, recovered by centrifugation, washed in 70% EtOH, dried and resuspended in 30 μl mung bean nuclease buffer (30 mM NaAc, pH 4.6, 300 mM NaCl, 1 mM ZnSO$_4$, 0.35 mM DTT, 2% glycerol) containing 25 units mung bean nuclease (Pharmacia Biotech). The single-stranded hair-pin DNA was clipped by incubating the reaction at 30° C. for 30 min., followed by addition of 70 μl 10 mM Tris-Cl, pH 7.5, 1 mM EDTA, phenol extraction and precipitation with 2 vols of 96% EtOH and 0.1 vol 3 M NaAc, pH 5.2 on ice for 30 min.

Blunt-end Formation with T4 DNA Polymerase

The double-stranded cDNAs were recovered by centrifugation and resuspended in 30 ml T4 DNA polymerase buffer (20 mM Tris-acetate, pH 7.9, 10 mM MgAc, 50 mM KAc, 1 mM DTT) containing 0.5 mM of each dNTP and 5 units T4 DNA polymerase (New England Biolabs, Beverly Mass., USA). The reaction mixture was incubated at 16° C. for 1 hour, and stopped by addition of EDTA to a final concentration of 20 mM, followed by phenol and chloroform extractions, and precipitation for 12 hours at −20° C. by addition of 2 vols 96% EtOH and 0.1 vol 3 M NaAc pH 5.2.

Adaptor Ligation, Not I Digestion and Size Selection

After the fill-in reaction the cDNAs were recovered by centrifugation, washed in 70% EtOH and dried. The cDNA pellet was resuspended in 25 μl ligation buffer (30 mM Tris-Cl, pH 7.8, 10 mM MgCl$_2$, 10 mM DTT, 0.5 mM ATP) containing 2.5 pg non-palindromic BstXI adaptors (Invitrogen Corp., San Diego Calif., USA) and 30 units T4 ligase (Promega Corp.) and incubated at 16° C. for 12 hours. The reaction was stopped by heating at 65° C. for 20 min. and then cooling on ice for 5 min. The adapted cDNA was digested with Not I (New England Biolabs) by addition of 20 μl water, 5 μl 10× Not I restriction enzyme buffer (New England Biolabs) and 50 units enzyme, followed by incubation for 2.5 hours at 37° C. The reaction was stopped by heating at 65° C. for 10 min. The cDNAs were purified by gel electrophoresis on a 0.8% SeaPlaque GTG low melting temperature agarose gel (FMC Corp. Bioproducts, Rockland ME, USA) in 1× TBE. The cDNAs were size-selected at a cut-off of 0.7 kb and recovered from the gel by use of b-Agarase (New England Biolabs) according to the manufacturer÷s instructions and precipitated for 12 hours at −20° C. by adding 2 vols 96% EtOH and 0.1 vol 3 M NaAc pH 5.2.

Construction of a CDNA Library

The directional, size-selected cDNAs were recovered by centrifugation, washed in 70% EtOH, dried and resuspended in 30 μl 10 mM Tris-Cl, pH 7.5, 1 mM EDTA. The cDNAs were desalted through a MicroSpin S-300 HR (Pharmacia Biotech) spin column according to the manufacturer's instructions. Three test ligations were performed in 10 μl ligation buffer (30 mM Tris-Cl, pH 7.8, 10 mM MgCl$_2$, 10 mM DTT, 0.5 mM ATP) containing 5 μl double-stranded cDNA (reaction tubes #1 and #2), 15 units T4 ligase (Promega) and 30 ng (tube #1), 40 ng (tube #2) and 40 ng (tube #3, the vector background control) of BstXI-NotI cleaved pYES 2.0 vector. The ligation procedure was incubation at 16° C. for 12 hours, followed by heating at 70° C. for 20 min. and addition of 10 μl water to each tube. One μl of each ligation mixture was electroporated into 40 μl electrocompetent E. coli DH10B cells (Life Technologies, Inc., Rockville Md., USA) as described by Sambrook, et al., supra.

Transformed E. coli were plated onto LB+ampicillin agar at a density resulting in 15,000–30,000 colonies/plate after incubation at 37° C. for 24 hours. A cell suspension was obtained by adding 20 ml LB+ampicillin to the plate, then shaken in a 50 ml tube for 1 hour at 37° C. Plasmid DNA was isolated from the cells using the QIAGEN plasmid kit (Qiagen GmbH, Hilden Del.) according to the manufacturers instructions, then stored at −20° C.

One-μl aliquots of purified plasmid DNA (100 ng/ml) from individual pools were transformed into S. cerevisiae W3124 by electroporation (Becker and Guarante, 1991. *Methods Enzymol*. 194: 182–187). The transformants were then plated on SC-agar containing 2% glucose and incubated at 30° C.

Identification of Positive Colonies

Colonies were screened indirectly for XET by finding xyloglucanase positive colonies. After 3–5 days of growth, the agar plates were replica plated onto SC-URA agar (with 20% galactose added) containing 0.1% AZCL xyloglucan ((Megazyme International Ireland Ltd., Bray County Wicklow, IE). The plates were incubated for 3–7 days at 30° C. Xyloglucanase-positive colonies were identified as colonies surrounded by a blue halo. Cells from enzyme-positive colonies were plated onto agar for single colony isolation, and an enzyme-producing single colony was selected from each of the xyloglucanase-producing colonies identified. All xyloglucanase positive colonies were tested for XET and were found to be positive.

Expression of XET in Aspergillus

An XET-producing yeast colony was inoculated into 20 ml YPD broth in a 50 ml glass test tube, then incubated with shaking for 2 days at 30° C. The cells were harvested by centrifugation, and the DNA isolated as described in WO 94/14953. Transformation of *E. coli* and isolation of plasmid DNA were performed using standard procedures. The cDNA insert was excised using the restriction enzymes BamH I and Xba I and ligated into the Aspergillus expression vector pHD414, resulting in the plasmid pA2XG80.

The cDNA inset of pA2XG80 was sequenced using the Taq deoxy-terminal cycle sequencing kit (Perkin Elmer, Foster City Calif., USA) and synthetic oligonucleotide primers on an ABI PRISM™ 377 DNA Sequencer (Applied Biosystems, Foster City, Calif., USA) according to the manufacturer's instructions.

The cDNA sequence encoding the XET gene is set forth in SEQ ID NO:1. The deduced amino acid sequence is set forth in SEQ ID NO:2.

Transformation of *Aspergillus Oryzae*

*Aspergillus niger* protoplasts were prepared as described in WO 95/02043, p. 16, line 21—page 17, line 12, which is hereby incorporated by reference. One hundred μl of protoplast suspension was mixed with 5–25 pg of the appropriate DNA in 10 μl of STC (1.2 M sorbitol, 10 mM Tris-HCl, pH 7.5, 10 mM CaCl$_2$). Protoplasts were then mixed with p3SR2 (a plasmid containing a gene for *A. nidulans* amds; Christensen, T., et al., 1988. Bio/Technology 6: 1419–1422) and incubated at ambient temperature for 25 minutes. 0.2 ml of 60% PEG 4000 (BDH 29576), 10 mM CaCl$_2$ and 10 mM Tris-HCl pH 7.5 was added and mixed, followed by adding and mixing in a second aliquot of 0.85 ml of the same solution, and a 25 minute incubation at room temperature. The mixture was centrifuged at 2500 g for 15 minutes and the pellet was resuspended in 2 ml of 1.2 M sorbitol. After a second sedimentation step the protoplasts were spread on minimal plates (Cove, 1966. Biochem. Biophys. Acta 113: 51–56) containing 1.0 M sucrose, pH 7.0, 10 mM acetamide and 20 mM CsCl. After incubation for 4–7 days at 37° C., spores were picked and spread for single colonies. This procedure was repeated to obtain spores of a single colony, which were then stored as defined transformants.

Positive transformants were confirmed by XET activity, assayed as described above, and by sequencing.

A clone, C1.XG80, containing the XET cDNA sequence was deposited at Deutsche Sammlung von Mikroorganismen und Zeilkulturen GmbH (DSMZ) on Feb. 24, 1998 under Accession No. DSM 12032.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A method for preparing a dough and/or a baked product made from dough, comprising incorporating into the dough a xyloglucan endotransglycosylase (XET).

2. The method of claim 1, wherein the XET is obtained from a plant or microbial source.

3. The method of claim 2, wherein the XET is obtained from a strain of Ascomycota.

4. The method of claim 1, wherein the XET is:
   (a) a polypeptide which is encoded by a nucleic acid sequence which hybridizes under medium stringency conditions with (i) the nucleic acid sequence set forth in SEQ ID NO: 1, (ii) its complementary strand, or (iii) a subsequence thereof;
   (b) a polypeptide having an amino acid sequence which has at least 50% identity with the amino acid sequence set forth in SEQ ID NO: 2;
   (c) a fragment of (a) or (b), wherein the fragment retains XET activity;
   (d) a polypeptide produced by a strain of *Tiarosporella phaseolina*; or
   (e) a polypeptide encoded by the XET encoding part of the cDNA sequence cloned into DSM 12032.

5. The method of claim 1, wherein the XET is incorporated in an amount of about 0.01 mg to about 100 mg per kilogram of dough.

6. The method of claim 1, wherein the XET is incorporated in an amount which is effective for increasing strength of the dough, increasing stability of the dough, reducing stickiness of the dough, improving machinability of the dough, increasing volume of the baked product, improving crumb structure of the baked product, improving softness of the baked product, improving flavour of the baked product, or reducing staling of the baked product.

7. The method of claim 1, wherein the dough is obtained from one or more ingredients selected from the group consisting of wheat meal, wheat flour, corn meal, corn flour, durum flour, rye meal, rye flour, oat meal, oat flour, soy meal, soy flour, sorghum meal, sorghum flour, potato meal, and potato flour.

8. The method of claim 1, wherein the dough is fresh or frozen.

9. The method of claim 1, wherein the baked product is selected from the group consisting of a bread, a roll, a French baguette-type bread, a pasta, a noodle, a pizza, a pita bread, a tortilla, a taco, a cake, a pancake, a biscuit, a cookie, a pie crust, steamed bread, and a crisp bread.

10. The method of claim 1, further comprising incorporating one or more additional enzymes selected from the group consisting of an amylase, a cellulase, a hemicellulase, a lipase, an oxidase, a pentosanase, a peptidase, a peroxidase, and a protease.

11. The method of claim 10, wherein the amylase is a *Bacillus stearothermophilus* maltogenic alpha-amylase.

12. The method of any of claim 1, further comprising incorporating one or more baking agents selected from the group consisting of a protein, an emulsifier, a granulated fat, an oxidant, an amino acid, a sugar, a salt, a flour, and a starch.

13. The method of claim 2, wherein the XET is obtained from a strain of Tiarosporella.

* * * * *